United States Patent
Neeson et al.

(10) Patent No.: US 6,343,510 B1
(45) Date of Patent: Feb. 5, 2002

(54) ULTRASONIC TESTING USING SYNTHETIC IMPULSES

(75) Inventors: Ian A. Neeson, Maitland; Leon C. Vandervalk; Andre D. Chevrier, both of Brockville, all of (CA)

(73) Assignee: VN Instruments Limited (CA)

( * ) Notice: Subject to any disclaimer, the term of this patent is extended or adjusted under 35 U.S.C. 154(b) by 0 days.

(21) Appl. No.: 09/298,259

(22) Filed: Apr. 22, 1999

(51) Int. Cl.[7] ............................................. G01N 29/00
(52) U.S. Cl. ........................................ 73/602; 73/659
(58) Field of Search ..................... 73/602, 603, 606, 73/607, 659

(56) References Cited

U.S. PATENT DOCUMENTS 4,317,369 A * 3/1982 Johnson ...................... 73/607
4,662,222 A * 5/1987 Johnson ...................... 73/602
5,235,857 A * 8/1993 Anderson .................... 73/625
5,734,754 A * 3/1998 Parker ....................... 382/243

* cited by examiner

Primary Examiner—Hezron Williams
Assistant Examiner—Nashmiya Fayyaz
(74) Attorney, Agent, or Firm—Webb Ziesenheim Logsdon Orkin & Hanson, P.C.

(57) ABSTRACT

An ultrasonic testing method and apparatus which includes synthesizing impulse response images using specially constructed waveforms. The apparatus includes a waveform generator, transducers for transmitting and receiving the ultrasonic signals and a digital signal processor or computer for efficiently processing the captured signal data to form the desired impulse response signals.

4 Claims, 7 Drawing Sheets

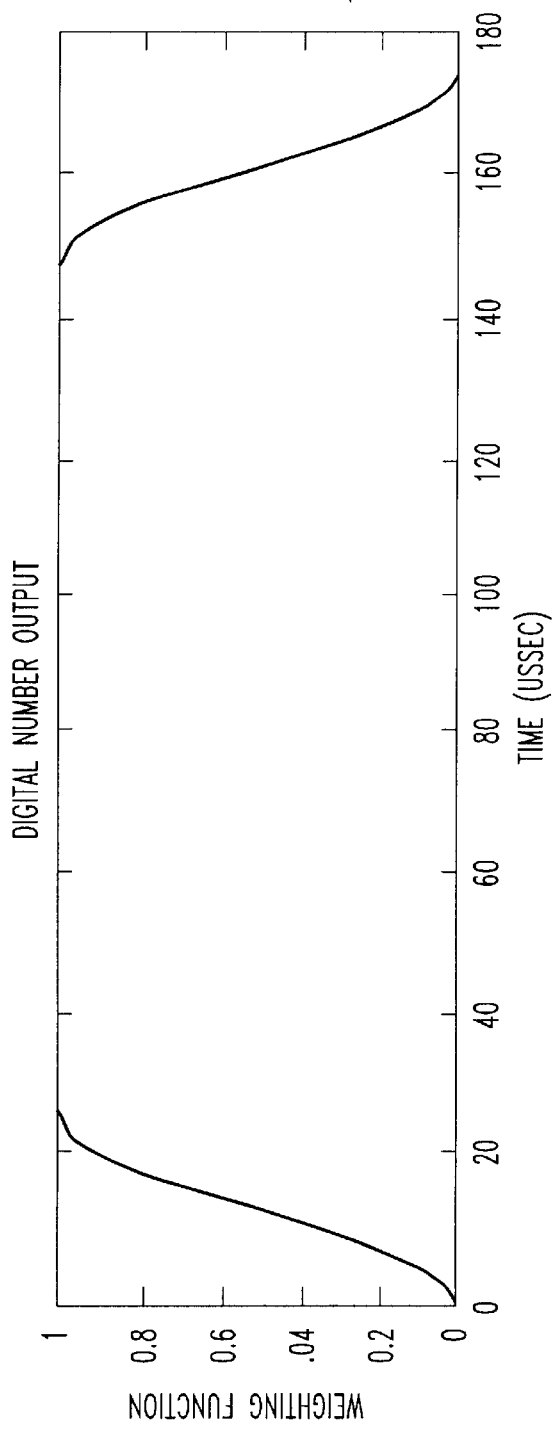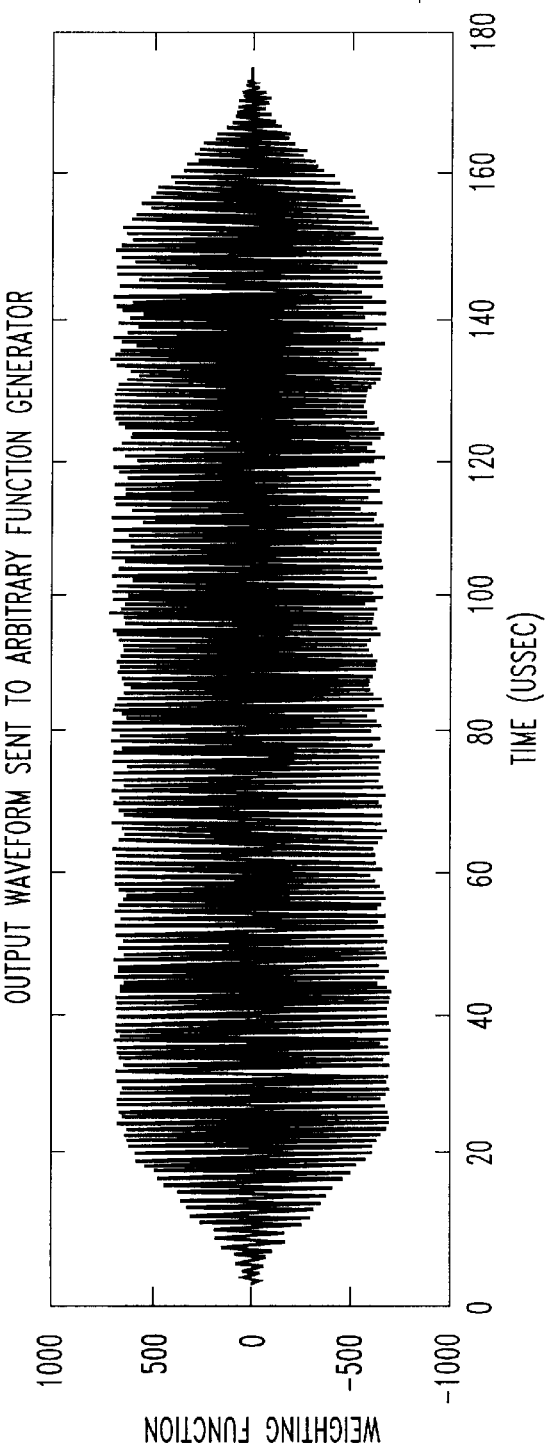
FIG.5a
FIG.5b

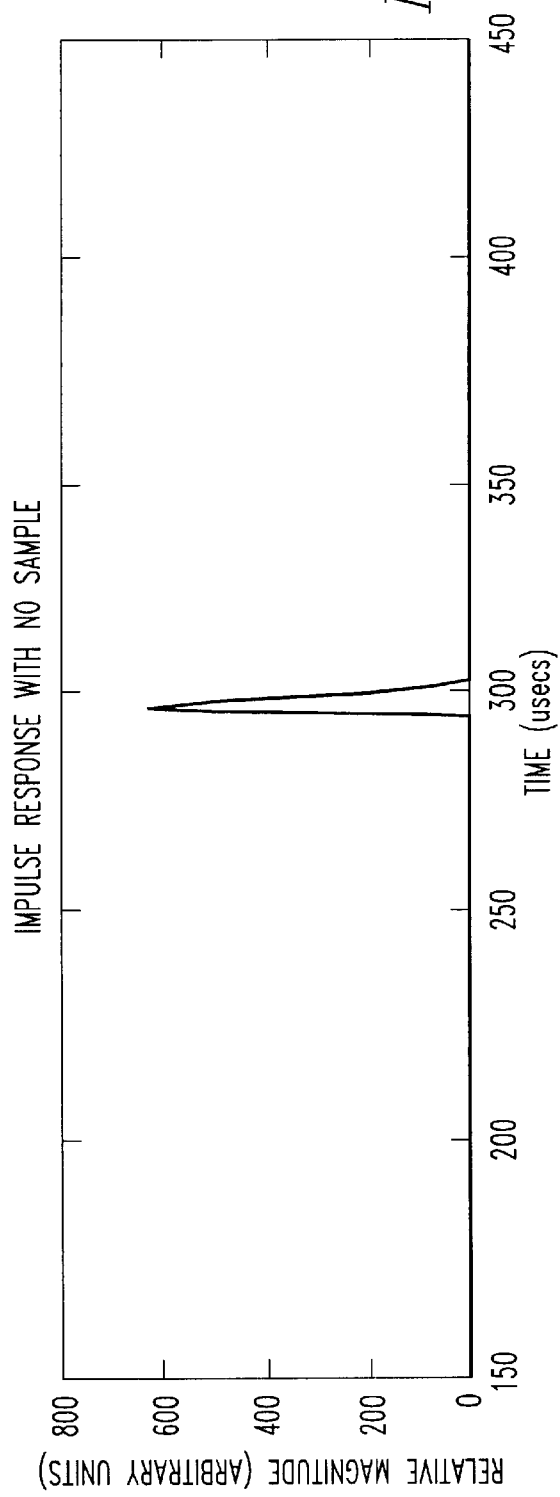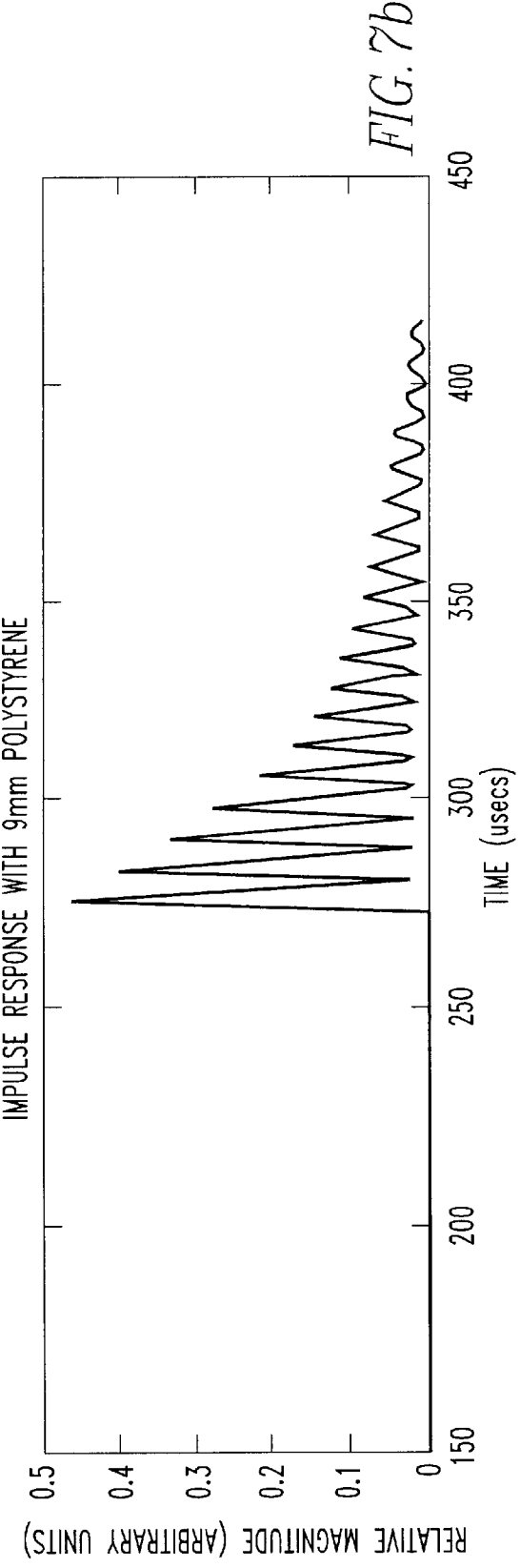

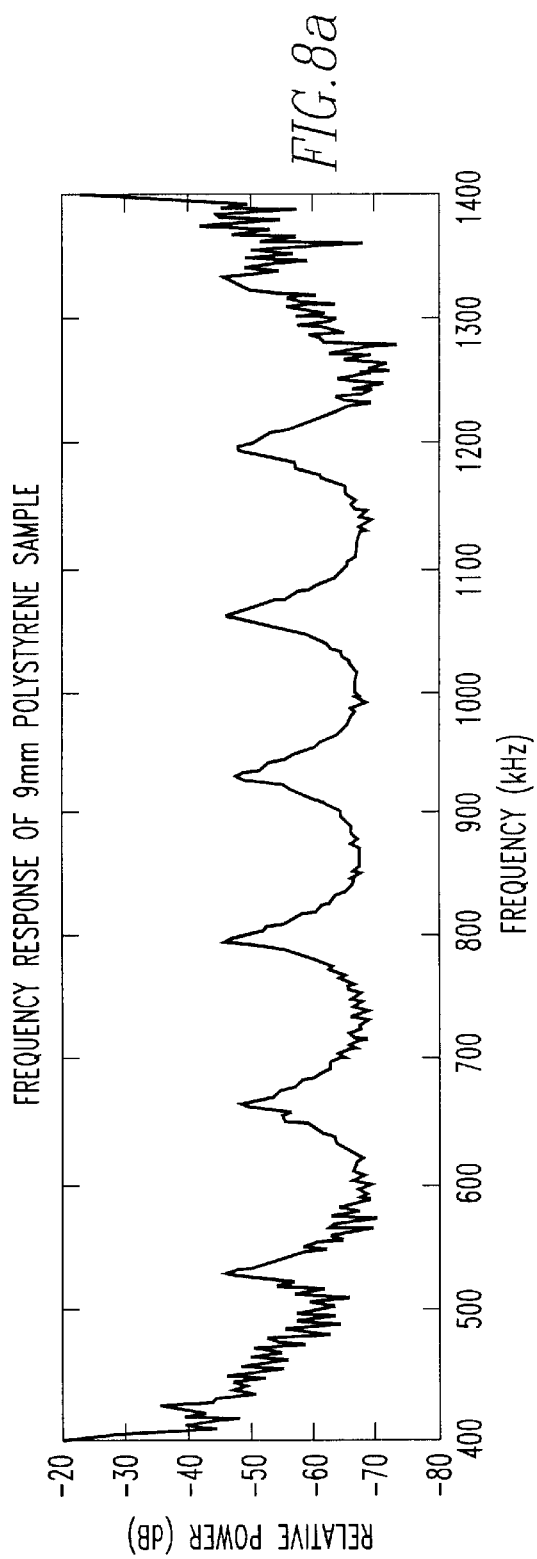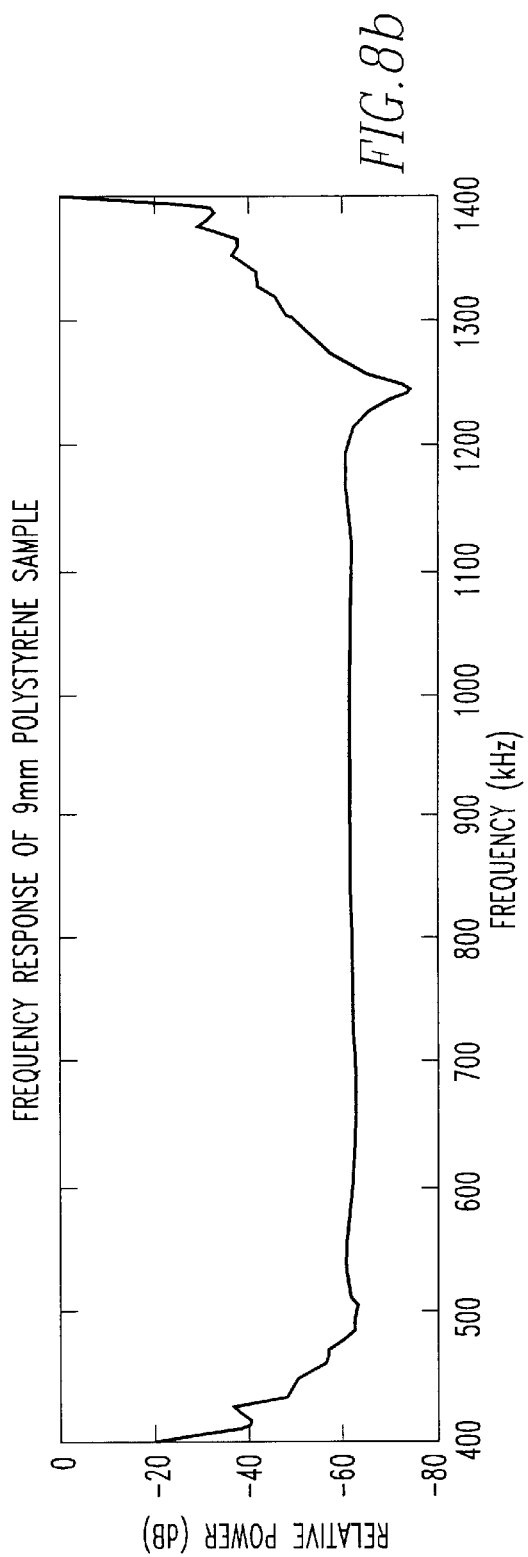

ULTRASONIC TESTING USING SYNTHETIC IMPULSES

BACKGROUND OF THE INVENTION

The application of ultrasonics to the analysis of material properties is constrained by physics and instrumentation. Advances in the application of ultrasound analysis have come through improvements to transducer sensitivity, focused devices and attempts to better match the transducer to the media being analyzed.

Using conventional techniques, the application of air-coupled ultrasonics has generally been regarded as impractical with a few specific exceptions. However, many applications where contact methods are not permitted are possible with air-coupled ultrasonics, such as the analysis of green ceramics, paper products and food products.

Conventional ultrasound testing is done using one of three modes of operation. The first mode uses a device known as a pulser to produce a high power impulse that is applied to an ultrasound transducer. An ultrasound pulse is then directed at a test piece. Typically, a transmitted or reflected pulse is captured and analyzed to determine the time of flight in the test piece. The second mode of operation involves continuous waves whereby a single frequency is applied to an ultrasound transducer. Again, a transmitted or reflected pulse is captured. The applied single frequency waveform is used as a reference to compare phase and amplitude of the captured ultrasound signals. The third mode of operation is a hybrid called a tone burst whereby a finite duration ultrasound signal is generated at a specific frequency. Tone burst signals are used in applications where stepped frequency response is desired or in pulse-echo applications where an infinite wave precludes using the same transducer to transmit and receive ultrasound.

There exist constraints on the amount of energy that can be used for ultrasonics. Any transducer has physical limits that cannot be exceeded without damaging the transducer itself. Furthermore, each transducer has a range over which it can produce an output that is linearly proportional to an input voltage within some frequency band. If this linear range is exceeded, the analysis of any captured or received signal is complicated by the non-linear nature of the sound source. The medium used to propagate sound waves, whether gas, liquid or solid, also has a finite limit to the linear sound pressure levels that can be sustained. In the case of solid materials, it is possible to damage or alter the material with the ultrasound which defeats the purpose of non-destructive testing.

With ultrasonic pulsers, a short duration voltage spike is presented to an ultrasound transducer and the resulting sound waves are propagated through the test piece or medium to a receiving transducer. Since a transducer is limited in the amount of energy that can be delivered in a single pulse, an upper limit exists on the attainable signal-to-noise ratio. In addition, as a pulse propagates through any medium, it is attenuated by the physical properties of the medium and by geometric factors related to beam spreading. As the distance traversed by a pulse increases, the amplitude of the received signal decreases.

Continuous wave systems typically use a lock-in amplifier to detect very weak signals while preserving the phase and amplitude information. These systems work very well in a laboratory setting, but due to the trade-off between integration time and sensitivity, they are limited to slow speed applications.

Tone burst systems have been employed to study ultrasonic resonance peaks associated with physical geometry. The concept involves stepping the frequency of a tone burst system to look for specific frequencies at which the amplitude is maximized or minimized. Tone burst methods can be applied to preserve phase and amplitude, however the time required to cover a useful frequency spectrum in detail can be prohibitive in practical applications. A resonance technique can provide information about thickness and velocity of a test sample provided the geometry is fairly simple and the internal structure is well known.

A method developed in other fields of study comprises an application of a time domain filter coupled with a specifically constructed waveform to yield a desired impulse response within the bandwidth limitations of the transducers. A wide bandwidth signal that meets specific criteria is constructed and used to synthesize an impulse response. The duration of the signal is arbitrary and does not affect the resolution of the system, therefore, a very long waveform representing very large total energy can be employed to compensate for boundary reflections, attenuation and geometric losses. We refer to a system using such a method as a synthetic impulse (or SI) system. An SI system preserves the phase of the waveform. The phase angle of the synthetic impulse can be used to precisely determine the time of flight to a tiny fraction of a wavelength. SI images can distinguish between two or more synthetic impulses by how the waveforms are coded. Independently coded waveforms make a number of applications possible.

It is a common misconception that improving time resolution necessarily implies increasing frequency. However, the time resolution of any signal is limited by the absolute bandwidth of the signal and not the frequency. Larger bandwidths generate improved time resolution. Attenuation in the propagation of ultrasound generally increases with frequency. An ideal ultrasonic analysis system should use broad bandwidth transducers at lower frequencies to improve time resolution while reducing losses.

SUMMARY OF THE INVENTION

It is an object of the present invention to provide methods of greatly enhancing the dynamic range, sensitivity and accuracy of ultrasonic measurements of material properties (either solid, liquid or gas) using ultrasonics in air-coupled, liquid-coupled or dry-coupled modes.

It is another object of the present invention to provide ultrasonic testing methods and apparatus using specially constructed waveforms and a time domain filter coupled to wide-band ultrasonic transducers.

It is a further object of the present invention to extract ultrasonic spectroscopic information about test materials in a fashion that separates the geometric properties from the acoustic properties.

It is yet another object of the present invention to provide means of compensating for air column losses in ultrasonic spectroscopy applications using information derived from synthetic impulse measurements.

It is the further object of the present invention to improve image quality in the Synthetic Aperture Focussing Technique (or SAFT).

It is the further object of the present invention to provide radial resolution with phased arrays to achieve angular resolution, thus forming two-dimensional images.

It is yet another object of the present invention to provide a practical method of compensating for air column fluctuations in air-coupled applications.

This invention relates generally to methods of creating, transmitting, receiving and processing ultrasound to enhance dynamic range, sensitivity and accuracy of measurement of ultrasonic signals. SI techniques are applied to contact ultrasonics and non-contact ultrasonics to boost sensitivity and dynamic range. The invention can be used to extend the capabilities of synthetic aperture focusing techniques and imaging methods based on array transducers.

Briefly, according to one embodiment of this invention, there is provided a method of measuring material properties using ultrasound comprising the steps for:
 a) generating a wide-band signal having a varying frequency waveform of fixed but arbitrary duration;
 b) storing a replica of the wide-band signal;
 c) applying the wide-band signal to an ultrasound transducer and directing the ultrasound generated by the transducer at a test piece;
 d) capturing a received signal being the ultrasound transmitted through or reflected from the test piece with an ultrasound transducer; and
 e) convolving the replica and the received signal to form one or more synthetic impulse images.

In another embodiment of this invention, there is provided a method of extracting ultrasound spectroscopic information from a test piece comprising the additional step of performing a Fourier transform on the synthetic impulse image and comparing it to the frequency spectrum of the wide-band signal. Preferably, air column error is determined by repeating the process with the specimen removed and the transducers moved closer together by the thickness of the specimen or by calculating the air column error.

According to yet another embodiment of this invention, there is provided an improved process for producing an image using the SAFT process comprising the steps for each individual reading required by the SAFT process comprising generating synthetic impulse images for each position at which a reading is taken.

According to yet another embodiment of this invention, there is provided a method of producing a two-dimensional image using an array of ultrasound transducers comprising the steps,
 for at least one transducer:
 a) generating a wide-band signal having a varying frequency waveform of fixed but arbitrary duration;
 b) storing a replica of the wide-band signal; and
 c) applying the wide-band signal to at least one ultrasound transducer and directing the ultrasound generated by the transducer at a test piece;
 for a plurality of transducers in the array:
 d) capturing a received signal being the ultrasound transmitted or reflected from the test piece;
 e) convolving the replica and the received signal to form one or more synthetic impulse images; and
 f) displaying a two-dimensional image based upon the synthetic impulse images and the coordinates of the transducers in the array.

According to a still further embodiment of this invention, there is a method of making air-coupled ultrasound measurements on a test piece comprising the steps for:
 a) generating a wide-band signal having a varying frequency waveform of fixed duration;
 b) storing a replica of the wide-band signal;
 c) applying the wide-band signal to an ultrasound transducer and directing the ultrasound generated by the transducer at a test piece;
 d) capturing a received signal being the ultrasound transmitted through the test piece with an ultrasound transducer;
 e) convolving the replica and the received signal to form one or more synthetic impulse images;
 f) removing the test piece and moving the transducers closer together by the thickness of the test piece and repeating steps a) to e) to determine the attenuating effects of the air column and instrumentation; and
 g) calculating the ratio of the specimen spectrum to the air column spectrum.

According to yet another embodiment, there is provided a method of making air-coupled ultrasound measurements on a test piece comprising the steps for:
 a) generating first and second different wide-band signals having a varying frequency waveform of fixed duration;
 b) storing a replica of each of the wide-band signals;
 c) applying the wide-band signals to spaced ultrasound transducers and directing the ultrasound generated by the transducers at a test piece;
 d) capturing a received signal being the ultrasound transmitted through the test piece and reflected signals returned from each surface of the test piece to respective transducers;
 e) convolving each of the replicas and the received signals to form synthetic impulse images for transmitted signals and signals reflected from each surface of the test piece;
 f) determining the air column attenuation from the synthetic impulses generated with the reflected signals; and
 g) calculating the ratio of the specimen spectrum to the air column spectrum.

Synthetic impulse output waveforms are constructed to distinguish one impulse from another. It is possible to construct an infinite number of different SI output waveforms that will exhibit almost no overlap unless the waveforms are identical. This approximates orthogonality in functional analysis. By creating two or more separate waveforms that are approximately orthogonal to one another, it is possible to recover two or more independent images concurrently. By choosing appropriate transducer arrangements, it is possible to excite different modes of vibration in a sample at the same time and then to process each mode separately. An example of separate SI waveforms is a first frequency ramped chirp running from low frequency to high frequency and a second orthogonal waveform being the frequency ramped chirp running from high frequency to low frequency.

BRIEF DESCRIPTION OF THE DRAWINGS

Further features and other objects and advantages of the invention will become apparent from the following detailed description made with reference to the drawings in which:

FIG. 5a illustrates a typical weighting function used to suppress side lobes in a preferred embodiment.

FIG. 5b shows the actual digital waveform presented to the digital-to-analog converter. This can also be used as a replica.

FIG. 7a is a graph that shows a transmission mode synthetic impulse image or response with no sample in place.

FIG. 7b shows the same configuration with a 9 mm polystyrene sample placed between the transducers.

FIG. 8a shows the frequency response of a 9 mm polystyrene sample determined by the methods of this invention.

FIG. 8b shows the frequency response of polystyrene determined by the methods of this invention.

DESCRIPTION OF THE PREFERRED EMBODIMENTS

This invention is directed to ultrasonics wherein virtual impulses are synthesized in the time domain by applying a coded waveform and convolving the captured result with a replica pulse captured in advance. Sensitivity and accuracy of measurements of signals propagating through a wide range of media are dramatically enhanced. These techniques can subsequently be applied to imaging methods, such as Synthetic Aperture Focusing and phased array imaging. This invention can be applied at any frequency and to any media. For air-coupled applications, practical constraints limit the application to less than 10 mHz. By substituting other gases and/or much higher gas pressures, it is possible to greatly extend this range. Using liquid coupling, such as water, much higher frequencies and resolutions can be obtained. In contact mode transducers, power amplifiers and digital signal acquisition and processing speeds are the limiting factors in the application of this invention.

To perform SI imaging and subsequent Synthetic Aperture Imaging, the instrumentation and transducers must meet certain criteria. They must be linear with respect to amplitude over a wide dynamic range. The transmitted and received waveforms must be synchronized with the possible exception of some jitter on any particular sample. The noise floor of the instrumentation must be low enough to allow useful signal processing. The power amplifiers used to drive the transducers must be capable of handling the unusual loads presented by ultrasonic transducers.

Figure 1:
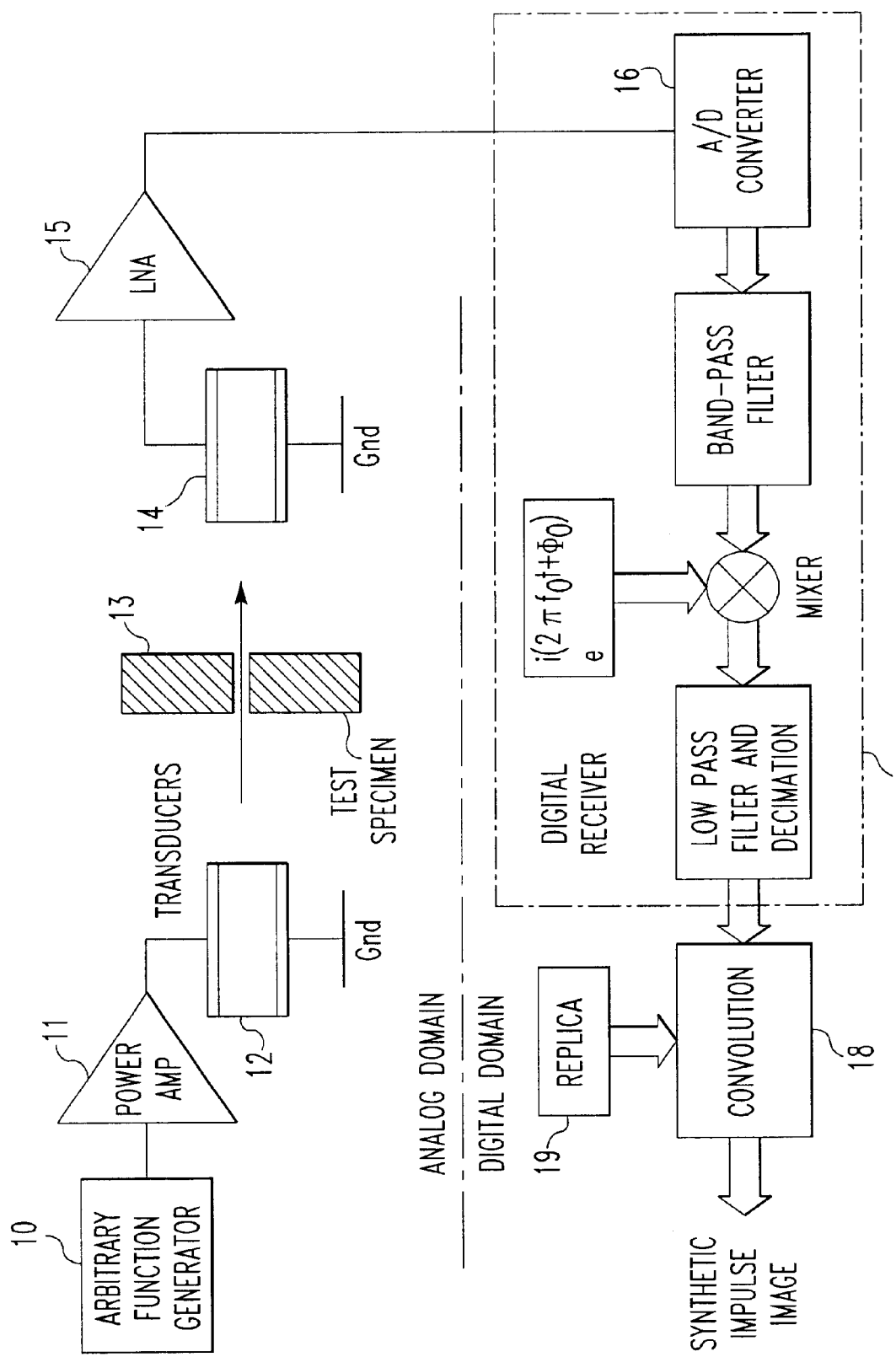
FIG. 1 is a schematic drawing showing the acoustic, electrical and digital signal paths used in a preferred embodiment of this invention. The top portion shows the analog signal path including the acoustic link between transmitter and receiver. The lower portion shows the digital signal path used to form the synthetic impulse images.

The general configuration of the preferred embodiment is shown in FIG. 1. An arbitrary function generator 10 for defining an output waveform is connected to a power amplifier 11 and then to an ultrasound transducer 12. The power amplifier 11 must be capable of delivering sufficient power over the entire bandwidth of the transducer 12. The ultrasonic signal having the waveform defined by the function generator is generated and transmitted through some medium and a test piece 13, then the signal is received by another transducer 14 (which can be the same as the transmitting transducer). The receiving transducer is connected to a high gain, low noise amplifier 15 that is used to boost the signal to a useful level. The amplified signal is fed to an analog-to-digital converter 16. The digital signal is then processed to form synthetic impulse images by digital receiver 17 and convolution computer 18 to which a replica from replica store 19 is provided. The signal from the convolution computer 18 is an impulse response signal comprising one or more synthetic impulse images.

Figures 2A, 2B, 2C, 2D:
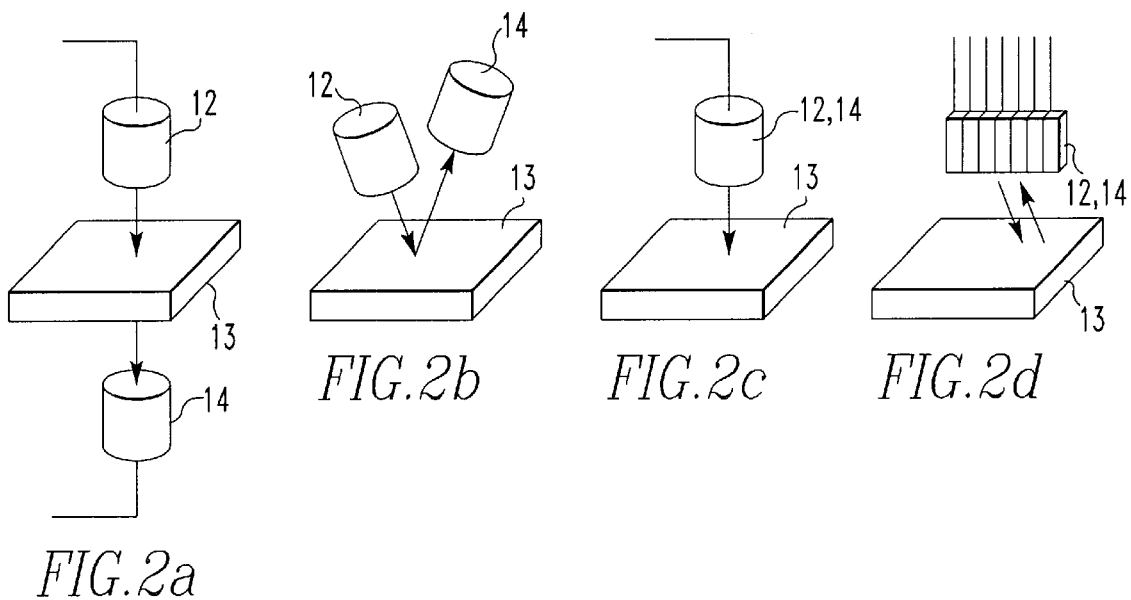
FIGS. 2a, 2b, 2c and 2d show the commonly used transducer configurations for materials testing.
Figure 3:
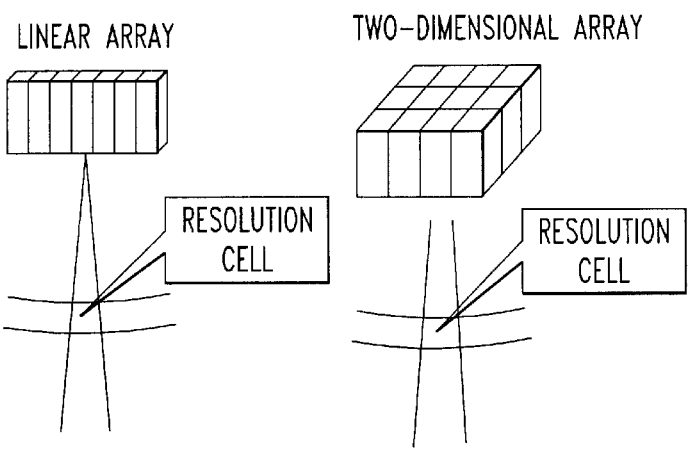
FIG. 3 illustrate how a resolution cell changes as a function of distance from the array. Both the two- and three-dimensional cases are shown.

FIG. 2a shows a transmission mode configuration where an ultrasonic signal is transmitted from one transducer, through a test specimen and to another transducer. FIG. 2b shows two transducers used in a reflection mode configuration. FIG. 2c shows a single transducer in a reflection mode configuration. FIG. 2d shows a generic array transducer in a reflection mode configuration. Two-dimensional arrays can also be used.

The arrangement of transducers for use with SI techniques can include two transducers facing one another with one acting as a sound source and the other acting as a receiver. The test material is placed between the transducers. The transducers can be set up such that the sound propagates into the test material at right angles to its surface or at arbitrary angles to study various propagation modes in the sample.

Two transducers can be located on the same side of the sample. The test material is placed in the field of view of the transducers and one transducer acts as a source and the other as a receiver.

A single transducer can act as both a source and a receiver. This mode requires the use of a diplexer to protect the sensitive receiver from the power amplifier used to drive the transducers.

An array transducer, for the purpose of beam forming, can replace a single element transducer. Array transducers provide alternate means of scanning or other possible imaging modes including tomography.

Figure 6:
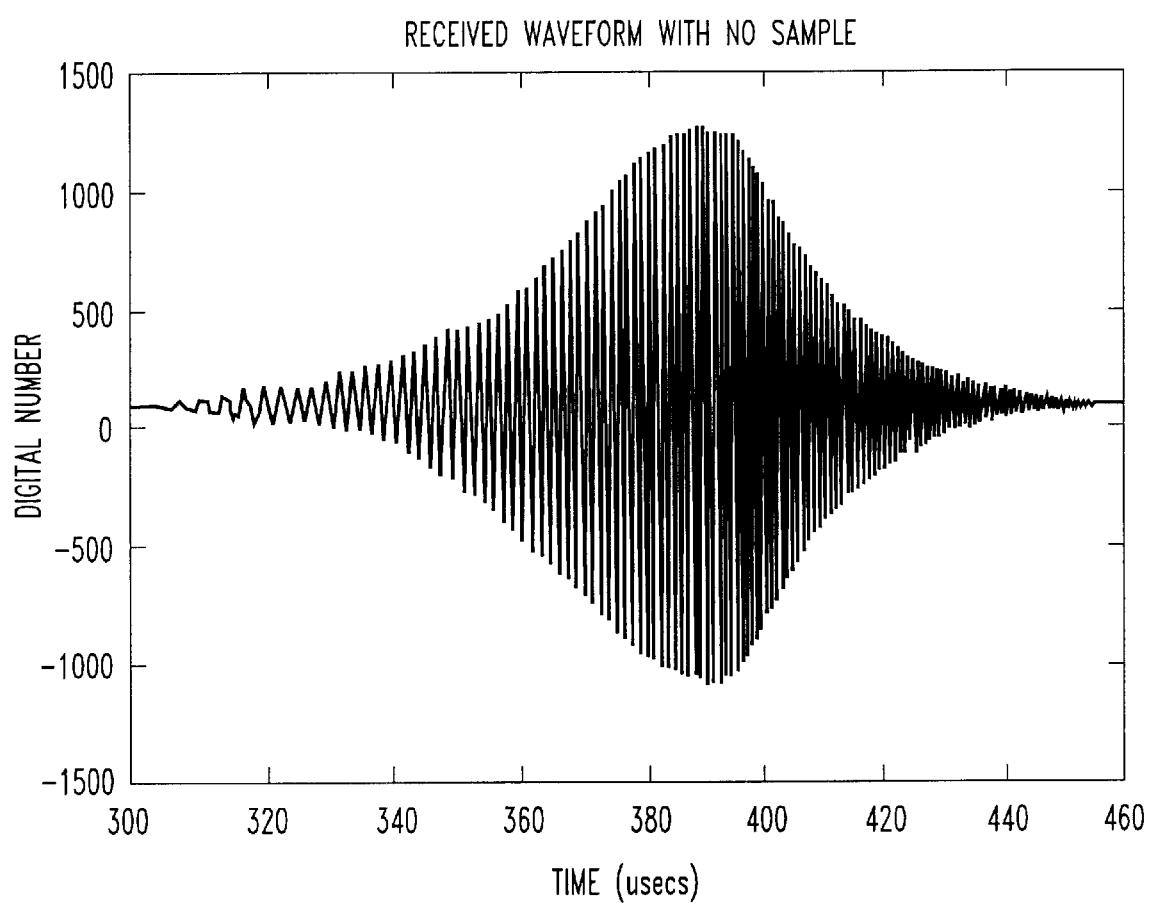
FIG. 6 is a graph that shows a typical received waveform with no sample in a transmission mode configuration. The frequency response of the waveform is limited by the transducer sensitivity and air column attenuation that increases with frequency. This waveform could be used as a replica.

A replica of an output waveform is captured and stored at 19 and used as a reference in the convolution processing. The replica can be captured by creating a model of the waveform or by copying the source waveform provided to the ultrasonic transducer 12, or by capturing a waveform that has been received by the same transducer or some other transducer placed in the acoustic signal path. FIG. 5b illustrates an output waveform sent to the transducer and FIG. 6 illustrates a received waveform with no sample. Either can be used as a replica waveform.

The function generator constructs special waveforms. The convolution of any such waveform with itself produces a delta function response. By an appropriate choice of waveform, it is possible to enhance the signal-to-noise ratio and improve the time resolution of the resulting impulse response. A waveform with the following general form is used.

$$V(t)=w(t) [A\sin\{f(t)t\}+B\cos\{f(t)t\}]$$

Where W(t) is a time dependent weighting function and, in the general case, A and B can also be time dependent. The function f(t) is a continuous and piecewise monotonic. The time t runs from time 0 to some arbitrary period T. For quadrature detection schemes, V(t) becomes complex.

$$V(t)=W(t) [A\cos(f(t)t+\phi)+iB\sin(f(t)t+\phi)]$$

In this case, $\phi$ is just a phase constant.

Weighting can be applied in terms of amplitude and time. Weighting functions applied as a function of time are typically used to suppress side lobes. A number of conventional weighting functions can be applied, including Hamming, Kaiser Bessel, Gaussian and many others. It is also possible to use the time-dependent frequency function f(t) to enhance or suppress spectral bands. If f(t)=at+b, then each frequency receives equal time. If the frequency function is non-linear, then more energy can be concentrated at selected frequency bands.

A synthetic impulse is a convolution of the replica or replicas with a received signal. If Vr(t) is the replica for a given configuration and VI(t) is the input (received signal) waveform, then the image S(t) is given by the following:

$$S(t)=Vr * VI$$

Where * denotes the convolution.

The resulting image is the ideal impulse response of the system acting on any material or materials placed in the field of view of the transmitting/receiving transducers. Synthetic impulse images preserve amplitude, phase, time of flight and the spectral and dispersion characteristics of any medium in the field of view of the transducer or transducers. By analyzing the images, it is possible to derive velocity, attenuation, dispersion and ultrasonic spectral features.

Figure 4:
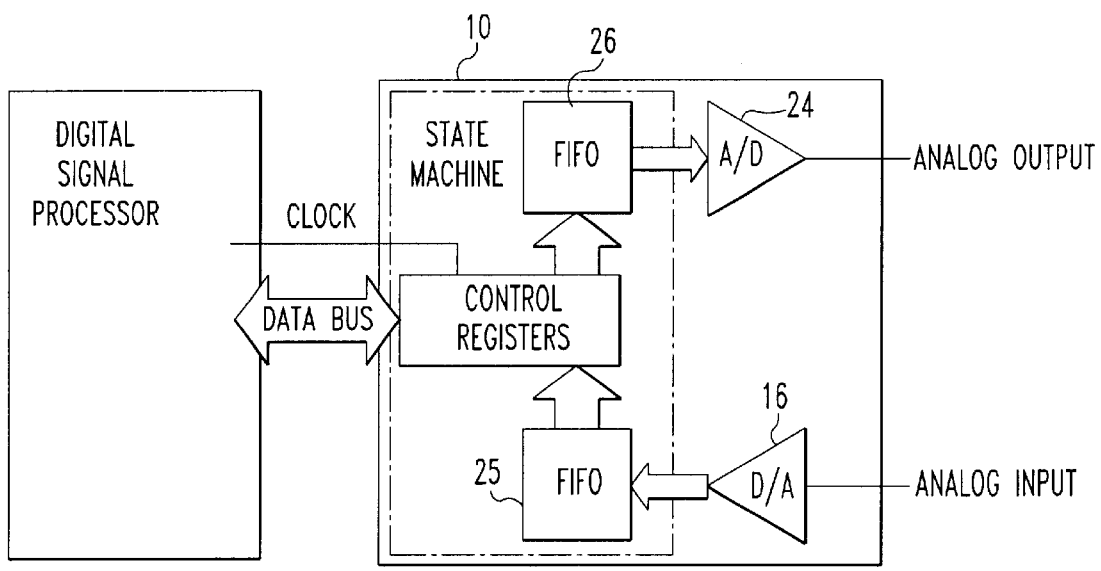
FIG. 4 is a schematic circuit diagram showing how the input and output signals are synchronized in a preferred embodiment.

The relative timing between the transmitted and received signals is extremely critical. Referring to FIG. 4, to assure proper synchronization, in the preferred embodiment, digital-to-analog circuit 24, which is part of the function generator 10, and analog-to-digital circuit 16 are linked by a common state machine. The state machine is a simple device that controls and synchronizes the transmission and reception of each discrete part of the analog waveform. FIG. 4 shows the internal configuration of this system.

The arbitrary function generator consists of two First In First Out (or FIFO) memory banks 25, 26 connected to digital-to-analog converter 16 and the analog-to-digital converter 24, respectively. The output FIFO is programmed or loaded by the digital signal processor with an appropriate waveform. A trigger signal directs the state machine to begin transmitting the waveform one point at a time. As each point is transmitted, the receiver digitizes one reading and stores the result in a second FIFO. The process of transmitting and digitizing continues until the entire output waveform has been transmitted. The state machine continues to digitize until some defined time limit has been reached. Once all the data has been acquired, the digital signal processor extracts the data from the input FIFO and then processes the data.

In the preferred embodiment, the digital signal processor can be connected to more than one transmitter-receiver at a time. This allows for multiple modes of operation concurrently or in an interleaved fashion.

An efficient processing algorithm and fast digital signal processing hardware are necessary to make synthetic impulse a practical tool. Two processing techniques are used to maximize throughput, a digital receiver and the Fourier convolution theorem.

A digital receiver is implemented which allows the data to be compressed into the minimum size necessary. The receiver is a quadrature detection scheme that is tuned to the center frequency of the output waveform. This produces a complex signal that can be properly represented by a sampling interval derived from the bandwidth of the source image alone.

The Fourier convolution theorem is used in conjunction with discrete fast Fourier transform. A discrete Fourier transform is applied to the calibration waveform and any received waveform. A vector multiply is done between the two resulting waveforms, then an inverse discrete Fourier transform is done to give the convolved signal.

The preferred embodiment uses a simple linear frequency ramp to generate the output waveform. The output waveform is constructed using the general function given previously with, A=0 and f(t)=at +b. The duration, amplitude and bandwidth of the output waveform are user-definable parameters. These parameters can be adjusted to match any particular set of transducers or to optimize transmission through some desired material. The weighting function W(t) is also user definable. In particular, the preferred embodiment uses a stepped cosine weighting function.

$$V(t)=W(t)[A\sin\{f(t)t\}+B\cos\{f(t)t\}]$$

Compensating for Air Column Changes

By definition, air-coupled ultrasonic applications must work in ambient air conditions that may include changes in temperature, humidity and pressure, as well as air movement and turbulence effects. Compensating for these effects is a significant problem. Using multiple orthogonal waveforms concurrently, the air column surrounding a material can be characterized at the same time the sample is measured. This is done by monitoring waveforms sent through the sample in both directions and also by monitoring waveforms reflected from each side of the sample.

A second technique relies on the use of a reference target placed on either side of the sample in a transmission mode configuration. This method uses the time of flight to each of the reference targets to estimate the change in time of flight in the air column. This data is used to refine estimates of velocity and thickness.

Ultrasonic Spectroscopy Using Synthetic Impulse

A technique has existed for measuring velocity or thickness accurately using resonant frequencies. A sound wave incident upon a flat sample will propagate through the sample until it reaches the far side. Part of the wave is reflected and part is transmitted through the boundary. The reflected wave returns to the top surface where some part is again reflected. At some frequency, the phase of the incident wave will coincide with the phase of the first reflected wave. FIG. 7a illustrates the impulse response of many reflections in a 9 mm polystyrene sample.

The velocity of sound in a sample may be inferred from resonance peaks that can be measured by applying ultrasonic energy to a material, provided the incident waveform has spectral components that encompass the resonant frequencies of the sample. The ultrasonic spectral properties of the material are included in the spectra, but are not easily extracted.

It is often desirable to study the acoustic spectral properties of a material independently of the geometry of the material. A synthetic impulse image preserves spectral characteristics and thus can be used to measure the ultrasonic spectrum of a test material. The first synthetic impulse through the material is gated and converted to the frequency domain using an FFT. Similarly, an air column synthetic impulse is converted to the frequency domain. If the sample thickness is small compared to the separation between the transducers, the attenuation as a function of frequency is given approximately by the ratio of the air column spectra to sample spectra. The resulting attenuation versus frequency curve includes two components (1) transmission coefficient and (2) attenuation versus frequency.

More precise spectral measurements are done by properly compensating for the air column attenuation versus frequency. One simple method that relies on an assumption about the stability of the air column is to simply increase the separation between transducers to exactly match the air column separation when measuring a test sample. A more sophisticated approach is to record images of the synthetic impulses as reflected from both surfaces and both transmission mode images. The sample spectra can be calculated by comparing the reflection mode spectra with the two transmission mode spectra. This method does not require moving transducers.

A synthetic impulse image preserves spectral characteristics and thus can be used to measure the ultrasonic spectrum of a test material. An air column synthetic impulse is collected and stored in memory. The reference air column SI data is converted to the frequency domain using an FFT. Next, a test material is introduced between the transducers. The first synthetic impulse through the material is selected. The first peak and the image data near it is preserved, all other image data is set to zero. The data is then converted to the frequency domain. If the sample thickness is small compared to the separation between the transducers, the attenuation as a function of frequency is given approximately by the ratio of the air column spectra to sample spectra.

A similar method can be applied to collect a reflection mode spectrum of a test surface. In this case, the reference spectra must be collected using a smooth surface. A surface is smooth provided the surface irregularities are much smaller than the acoustic wavelengths in air used to measure the surface.

Synthetic Aperture Image Formation

Synthetic Impulse methods are useful for synthetic aperture image formation. The processes of forming two-dimensional synthetic impulse images are a simple extension of one-dimensional imaging. A variety of processing schemes exist to perform a two-dimensional synthetic aperture, including a range Doppler method and a chirp scaling method. Synthetic aperture images offer all the advantages of synthetic impulse methods plus the added advantage of having a spatial resolution that is independent of the distance between the transducer and test material. By comparison, focused transducer imaging methods rely on very precise placement of the test sample with respect to the transducers.

Synthetic impulse methods can be used to extend the capabilities of tomography scanning systems. Such a device can be used to inspect irregularly-shaped parts in a non-contact mode. A combination of a synthetic impulse method with an array transducer can be used to form a practical two-dimensional scanning system. The distance from the array transducer is resolved using synthetic impulses, and the lateral displacement is resolved by steering the beam electronically. Beam steering is a straightforward application of small phase changes applied across a linear array.

The applications and benefits of SI are as follows: A synthetic impulse image distributes the information content over a potentially large signal. Any small region of the signal may be subject to noise, interference or even signal loss without significantly damaging the whole. An SI system preserves the phase of a synthetic impulse. The phase angle of the pulse can be used to very precisely determine the time of flight to a very small fraction of a wavelength. SI images preserve amplitude that makes analytical analysis of SI image data very simple and very accurate. SI images provide a simple means of determining reflection coefficients, transmission coefficients and attenuation constants. The wide dynamic range and linearity of SI images allow for very precise spectral analysis of materials using contact or non-contact ultrasonic techniques. Information about the spectral characteristics of the material content of the sample can be derived by an analysis of the time domain impulse through the material. Sample geometry can be inferred by a spectral analysis of the time domain images of multiple reflections in the sample. Velocity, as a function of frequency in a material, can be determined by an appropriate spectral analysis.

SI techniques can also be applied to synthetic aperture focusing to greatly improve the accuracy and quality of image data. The synthetic impulse algorithm can be implemented in a variety of ways including a range Doppler technique and a chirp scaling method.

A combination of phased arrays, SI processing and synthetic aperture focusing can be employed to form three-dimensional images of a sample with a single linear pass of the transducers.

Having thus defined our invention in the detail and particularity required by the Patent Laws, what is desired protected by Letters Patent is set forth in the following claims.

What is claimed:

1. A method of measuring properties of a solid test subject using ultrasound comprising the steps for:
    a) generating a wide-band signal having a coded varying frequency waveform of fixed but arbitrary duration such that when convolved with itself will produce an approximation of an ideal impulse response of an ultrasound system;
    b) storing a replica of the wide-band signal;
    c) applying the wide-band signal to an ultrasound transducer and directing the ultrasound generated by the transducer at the test subject;
    d) capturing a received signal being the ultrasound transmitted through or reflected from the test subject with an ultrasound transducer time referenced to the signal in step c); and
    e) convolving the replica and the received signal to form one or more synthetic impulse images of said solid test subject, whereby measurement of properties of the test subject may be enhanced.

2. A method of extracting ultrasound spectroscopic information from a test subject having a width aligned between first and second ultrasound transducers comprising the steps for:
    a) generating a wide-band signal having a varying frequency waveform of fixed but arbitrary duration such that when convolved with itself will produce an approximation of an ideal impulse response of an ultrasound system;
    b) storing a replica of the wide-band signal;
    c) applying the wide-band signal to a first ultrasound transducer and directing the ultrasound generated by the first transducer at the test subject through a fluid medium;
    d) capturing a received signal being the ultrasound transmitted through or reflected from the test subject with a second ultrasound transducer time referenced to the signal in step c);
    e) convolving and storing the replica and the received signal to form a synthetic impulse image of said test subject; and
    f) performing a Fourier transform on the synthetic impulse image and dividing the Fourier transform by the Fourier transform of the replica of the wide-band signal stored in step d), whereby measurement of properties of the test subject may be enhanced.

3. The method according to claim 2, wherein any error caused by the fluid medium is determined by repeating the method of claim 2 with the test subject removed and moving the first and second transducers closer together by said width of the test subject.

4. The method according to claim 2, wherein any error caused by the fluid medium is calculated.

* * * * *

UNITED STATES PATENT AND TRADEMARK OFFICE
CERTIFICATE OF CORRECTION

PATENT NO.    : 6,343,510 B1
DATED         : February 5, 2002
INVENTOR(S)   : Ian A. Neeson et al.

It is certified that error appears in the above-identified patent and that said Letters Patent is hereby corrected as shown below:

<u>Column 10,</u>
Line 56, "in step d)" should read -- in step b) --.

Signed and Sealed this

Tenth Day of September, 2002

*Attest:*

*Attesting Officer*

JAMES E. ROGAN
*Director of the United States Patent and Trademark Office*